United States Patent
Käkönen et al.

(10) Patent No.: US 6,967,081 B1
(45) Date of Patent: Nov. 22, 2005

(54) METHOD FOR PREDICTION OF BONE FRACTURES BY OSTEOCALCIN MEASUREMENTS

(76) Inventors: Sanna-Maria Käkönen, Murtomaantie 39, Turku (FI) 20300; Heikki Luukinen, Purantje 17 D 16, Oulu (FI) 90240; Kim Pettersson, Tiilentekijänkatu 14 E 20, Turku (FI) 20810; Timo Lövgren, Yliopistonkatu 2 H 155, Turku (FI) 20100; H. Kalervo Väänänen, Kannuskatu 13 J 143, Turku (FI) 20880

( * ) Notice: Subject to any disclaimer, the term of this patent is extended or adjusted under 35 U.S.C. 154(b) by 0 days.

(21) Appl. No.: 09/937,620

(22) PCT Filed: Mar. 20, 2000

(86) PCT No.: PCT/FI00/00227

§ 371 (c)(1),
(2), (4) Date: Feb. 4, 2002

(87) PCT Pub. No.: WO00/58732

PCT Pub. Date: Oct. 5, 2000

(30) Foreign Application Priority Data

Mar. 29, 1999 (FI) .................................... 990693

(51) Int. Cl.⁷ ............................................ G01N 33/53
(52) U.S. Cl. .................. 435/7.9; 435/7.93; 435/70.21; 435/810; 436/514; 436/506
(58) Field of Search ................................ 435/7.9, 7.93, 435/70.21, 810; 436/514, 506

(56) References Cited

FOREIGN PATENT DOCUMENTS

| DE | 4 008 546 A1 | 3/1989 |
|---|---|---|
| EP | 0 557 663 A1 | 1/1993 |
| WO | WO 99/09058 | 2/1999 |

OTHER PUBLICATIONS

Koyama et al. J. Immunological Methods 1991 vol. 139: 17-23 (Abstract).*
Obrant, Karl J. et al., "The Proportion of Carboxylated to Total or Intact Osteocalcin in Serum Discriminates Warfarin-Treated Patients from Control Subjects," *J. Bone and Mineral Res.* 4:555-569 *(1888), with abstract.
BIOSIS Abstract No. 92041118 (1991).
BIOSIS Abstract No. 206737 (1998).
CAPLUS Abstract No. 812331 (1997).

* cited by examiner

*Primary Examiner*—Long V. Le
*Assistant Examiner*—Jacob Cheu
(74) *Attorney, Agent, or Firm*—Rothwell Figg Ernst & Manbeck (57) ABSTRACT

This invention concerns a method for the assessment of bone fragility and fracture risk, or osteoporosis, in a person. In said method, the concentration of gamma-carboxylated osteocalcin (COC) and optionally also the concentration of intact or total osteocalcin (IOC or TOC, respectively) in a body fluid sample of said person is measured. The concentration of gamma-carboxylated osteocalcin (COC) so obtained is compared to the mean concentration of gamma-carboxylated osteocalcin (mean COC) in similar body fluid samples of the population of the same age and sex. Alternatively, the determined ratio COC/IOC or COC/TOC for said person, is compared to the mean ratio COC/IOC or COC/TOC, (mean ratio COC/IOC or mean ratio COC/TOC) determined from measurements in similar body fluid samples of the population of the same age and sex. A measured COC that is lower than the mean COC is used as indication of osteoporosis, bone fragility or increased risk of bone fracture in said person. Preferably, a determined ratio COC/TOC that is lower than the mean ratio COC/TOC is used as indication of osteoporosis, bone fragility or increased risk of bone fracture in said person. The invention concerns further kits for use in the assessment according to this invention.

8 Claims, 2 Drawing Sheets

METHOD FOR PREDICTION OF BONE FRACTURES BY OSTEOCALCIN MEASUREMENTS

FIELD OF INVENTION

This invention relates to a method for the assessment of bone fragility and fracture risk, and osteoporosis, using a as marker a quantitative determination of circulating γ-carboxylated human osteocalcin (hOC) or the ratio γ-carboxylated to total hOC or to intact hOC concentration.

INTRODUCTION AND BACKGROUND

The publication and other materials used herein to illuminate the background of the invention, and in particular, cases to provide additional details respecting the practice, are incorporated by reference.

Human osteocalcin (hOC), also designated bone Gla protein (BGP), is the most abundant noncollagenous protein synthesized by bone osteoblast (Poser et. al. J Biol Chem 1980; 255: 8685–91). Although most of the synthesized osteocalcin is absorbed to bone hydroxyapatite by γ-carboxylated glutamic acids (Gla), a small part of it leaks into the blood stream where it can be detected (Price et al. J Biol Chem 1981; 256: 12760–6). Part of the hOC found in blood is also thought to originate from the resorption process, when the hOC inside the bone tissues is released during bone degradation (Gundberg and Weinstein J Clin Invest 1986; 77: 1762–7). Levels of circulating hOC have been widely used in the clinical investigations as a marker of bone formation (Power and Fottrell Crit Rev Clin Lab Sci 1991; 28: 287–335) and serum hOC levels have been shown to correlate with bone mineral density measurements in many situations (Yasamura et al. J Clin Endocrinol Metab 1987; 64: 681–5).

The discordant results obtained from different hOC assays have hindered widespread usage of hOC in clinical applications (Masters et al. Clin Chem 1994; 40: 358–63, Deftos et al. Clin Chem 1992; 38: 2318–21, Delmas et al. J Bone Miner Res 1990; 5: 5–11 and Diego et al. 1994; 40: 2071–7). This phenomenon could partly be explained due to different assay formats i.e. sandwich vs. competitive assays or due to different detection techniques. Presently no calibration standard is available. However, even if the same standard preparation is used, hOC levels measured in different laboratories cannot be directly compared (Delmas et al. J Bone Miner Res 1990). The diversity of hOC molecule itself in circulation has an evident contribution to its immunoreactivity in various assays. The vitamin K dependent γ-carboxylation degree of the glutamic acid residue varies (Poser et. al. J Biol Chem 1980; 255: 8685–91). Impairment γ-carboxylation of hOC purified from bone has been indicated by Cairns and Price, J Bone Min Res 1994; 9: 1989–97 and confirmed in our studies (Hellman et al. J Bone Miner Res 1996; 11: 1165–75). When $Ca^{2+}$ binds to Gla residues an α-helix structure is known to form (Hauschka and Carr, Biochemistry 1982; 21: 2538–47 and Atkinson et al. Eur J Biochem 1995; 232: 515–21). Upon removal of $Ca^{2+}$ with EDTA this helical conformation is destroyed. The conformation of decarboxylated OC lies somewhere between the random coil and helical form. Thus, in solution the peptide occurs as a flexible structure and a single conformation cannot be defined for it (Atkinson et al. Eur J Biochem 1995; 232: 515–21). Peptide bonds between arginine residues 19 and 20 and between residues 43 and 44 are susceptible to tryptic hydrolysis leading to peptides 1–19, 20–43, 45–49, 1–43, and 20–49 which may be the main products of hOC breakdown in the circulation (Farrugia and Melick, Calcif Tissue Int 1986; 39: 234–8, Hellman et al. J Bone Miner Res 1996; 11: 1165–75 and Garnero et al. J Bone Miner Res 1994; 9: 255–4). Multiple immunoreactive forms of hOC have been discovered in circulation (Garnero et al. J Bone Miner Res 1994; 9: 255–4) and also in urine (Matikainen et al. J Bone Miner Res 1999; 14: 431–8, Taylor et al. J Clin Endocrin Metab 1990; 70: 467–72). The fragments of hOC can be produced either during osteoclastic degradation of bone matrix or as the result of the catabolic breakdown of the circulating protein after synthesis by osteoblasts.

The degree of vitamin K-dependent γ-carboxylation in the glutamic acid residues varies, so the circulating hOC is a pool of hOC molecules with variable γ-carboxylation (Cairns and Price J Bone Min Res 1994; 9: 1989–97). During the recent years the relevance of the γ-carboxylation degree of osteocalcin for predicting the bone turnover status has been investigated. Osteocalcin is known to be attached to the bone mineral content, hydroxyapatite, by γ-carboxylated glutamic acids. Hydroxyapatite has thus been used to distinguish the fully γ-carboxylated form of protein from non- or undercarboxylated (uchOC) forms (Price et al. J Biol Chem 1981; 256: 12760–6). The hydroxyapatite binding capacity of the circulating osteocalcin has been reported to be abnormally low in elderly people when compared to the premenopausal group (Knapen et al. Ann Intern Med 1989; 111: 1001–5, Merle and Delmas Bone Miner 1990; 11: 237–45). Szulc et al. (J Clin Invest 1993; 91: 1769–74, J Bone Miner Res 1994; 9: 1591–5, Bone 1996; 18: 487–8) have shown that circulating uchOC is a marker of the risk of hip fracture in a population of institutionalized women and that the BMD (bone mineral density) is significantly decreased in women with elevated uchOC. However, the hydroxyapatite-based assays provide only a crude estimation of the degree of carboxylation. Complete separation of the two forms is difficult due to incomplete binding of carboxylated forms at lower concentrations and particularly because of nonspecific binding of undercarboxylated osteocalcin at higher concentrations (Merle and Delmas Bone Miner 1990; 11: 237–45, Käkönen et al. Protein Expres Purif 1996; 8: 137–44, Szulc et al. J Clin Invest 1993; 91: 1769–74). Moreover, the methods could be sensitive to changes in buffer conditions and quality of the hydroxyapatite reagents employed. Gundberg et al. showed that N-terminal binds lower. Recently, Vergnaud et al. (J Clin Endocrinol Metab 1997; 82: 719–24) developed a new ELISA for uchOC based on Mabs, with low cross-reactivity to carboxylated hOC. Using this specific immunoassay they showed that uchOC, but not total hOC, predicted hip fracture risk independently of bone mass in elderly women drawn from the general population. Osteoporotic fractures have serious consequences among the elderly. They result in high mortality, frequent hospitalization, high health care costs, functional impairment, pain and reduced quality of life (Ross Arch Intern Med 1996; 156: 1399–411). Therefore, easily implemented valid methods to assess the risk of fracture are needed.

Low bone density predicts the occurrence of fracture (Hui et al. Ann Intern Med 1989; 111: 355–61, Melton et al. J Bone Miner Res 1993; 8: 1227–33) and hip fracture (Cummings et al. Lancet 1993; 341: 72–5). Serum osteocalcin as a measure of increased bone turnover is a determinant of osteoporosis in postmenopausal women, and the serum concentrations of osteocalcin increase with advancing age (Garnero et al. J Bone Miner Res 1996; 11: 337–49, Melton et al. J Bone Miner Res 1997; 12: 1083–91), in both men and women (Epstein et al. Lancet 1984; 307–10) Results concerning the relationship between osteocalcin and the occurrence of fracture are contradictory, as some authors suggest that there is a positive association (Riis et al. Bone 1996; 19: 9–12), while others suggest that there is no association (Åkesson et al. J Bone Miner Res 1995; 10: 1823–9, Garnero et al. J Bone Miner Res 1996; 11: 1531–8).

The degree of the vitamin K-dependent γ-carboxylation of osteocalcin (Plantalech et al. J Bone Miner Res 1991; 6: 1211–6, Obrant et al., J Bone Miner Res 1999; 14: 555–60) becomes reduced with aging (Knapen et al. Ann Intern Med 1989; 111: 1001–5, Merle and Delmas Bone Min 1990; 11: 237–45) and by affecting the calcium-binding capacity of the protein may lead to osteopenia (Pastoreau et al. J Bone Miner Res 1993; 8: 1417–26). In line with these findings, high proportions of under-carboxylated osteocalcin are associated with the occurrence of hip fractures in the institutionalized elderly (Szulc et al. J Clin Invest 1993; 91: 1769–74). This finding was supported by the results of a case-control study within a large prospective study among healthy elderly community-living women (Vergnaud et al. J Clin Endocrinol Metab 1997; 82: 719–24).

SUMMARY OF THE INVENTION

According to one aspect, this invention concerns a method for the assessment of bone fragility and fracture risk, or osteoporosis, in a person, comprising the steps of
a) measuring the concentration of gamma-carboxylated osteocalcin (COC) and optionally also the concentration of total osteocalcin (TOC) or intact osteocalcin (IOC) in a body fluid sample of said person,
b) comparing
  i) the concentration of gamma-carboxylated osteocalcin (COC) so obtained to the mean concentration of gamma-carboxylated osteocalcin (mean COC) in similar body fluid samples of the population of the same age and sex, or
  ii) the determined ratio COC/TOC or COC/IOC for said person to the mean ratio COC/TOC (mean ratio COC/TOC) or COC/IOC, respectively determined from measurements in similar body fluid samples of the population of the same age and sex, and
c) using
  i) a measured COC that is lower than the mean COC as indication of osteoporosis, bone fragility or increased risk of bone fracture in said person, or
  ii) the determined ratio COC/TOC or COC/IOC that is lower than the mean ratio COC/TOC or COC/IOC, respectively as indication of osteoporosis, bone fragility or increased risk of bone fracture in said person.

According to another aspect, this invention concerns a kit for the assessment of bone fragility and bone fracture risk, or osteoporosis in a person, comprising a capture reagent consisting of at least one monoclonal or polyclonal antibody or fragment thereof, said antibody or fragment being specific for gamma-carboxylated osteocalcin in a body fluid sample of said person, and a detecting reagent, capable of detecting the complex formed between the capture reagent and the antigen.

DETAILED DESCRIPTION OF THE INVENTION

Easily implemented and valid methods are needed for the assessment of fracture risk among the elderly. The serum intact, total and γ-carboxylated hOC were measured by osteocalcin immunofluorometric assays in 792 home-dwelling persons of 70 years or older by one-step two-site immunofluorometric assays. The occurrence of fractures was followed for five-years. The serum γ-carboxylated hOC and especially, the ratio γ-carboxylated to total hOC or γ-carboxylated to intact hOC predicted the occurrence of fractures independently on other baseline subject-related risk factors of fractures. The relative risk was highest in the population older than 80 years and the predictive value lasted three years. The measurement of the ratio is an easily implemented and valid method for the assessment of fracture risk among the elderly.

In this invention, the term "intact osteocalcin" or IOC in a persons body fluid sample shall be understood to include the full length fragment of the osteocalcin molecule, irrespective of its gamma-carboxylation. The term "total osteocalcin" or TOC in a persons body fluid sample shall be understood to include the full length and/or a large $NH_2$-terminal fragment of the osteocalcin molecule, irrespective of its gamma-carboxylation. The term "gamma-carboxylated osteocalcin" or COC includes mono-, di- and tricarboxylated osteocalcins, but not uncarboxylated forms of osteocalcin. Suitable body fluids for the measurement of these markers are e.g. serum, plasma or urine.

A person can be considered to belong to a group with susceptibility to osteoporosis, bone fragility or increased risk of bone fracture if said person's body fluid concentration of gamma-carboxylated osteocalcin is lower than the mean concentration of gamma-carboxylated osteocalcin in similar body fluid samples of the population of the same age and sex. An even more preferable marker is the ratio "gamma-carboxylated osteocalcin to total osteocalcin" (COC/TOC) or "gamma-carboxylated osteocalcin to intact osteocalcin" (COC/IOC). If the person has a COC/TOC or COC/IOC value that is lower than the mean COC/TOC value or COC/IOC value of the population of the same age and sex, then the person belongs to a group with susceptibility to osteoporosis, bone fragility or increased risk of bone fracture.

The term antibody "fragment" shall be understood to mean a recombinantly or proteolytically produced antibody fragment.

The gamma-carboxylated osteocalcin (COC) is preferably measured by means of at least one monoclonal or polyclonal antibody or fragment thereof, wherein said antibody or fragment is specific for gamma-carboxylated osteocalcin. Preferable, one monoclonal antibody or fragment thereof, or a mixture of several monoclonal antibodies or fragments thereof are used for recognizing any one of the epitopes specific for gamma-carboxylated osteocalcin. Preferably, the antibody or fragment recognizes an epitope occurring in the region of the amino acids 17–24 of the gamma-carboxylated osteocalcin molecule. According to another preferred embodiment, the antibody or fragment recognizes the tertiary structure associated with the gamma-carboxylated osteocalcin.

The specificity of the antibody or fragment for gamma-carboxylated osteocalcin can be dependent on the presence of bivalent metal ions, such as $Ca^{2+}$. The specificity either decreases or increases in the presence of said metal ions.

The detecting reagent shall be understood as a labelled monoclonal or polyclonal antibody or fragment thereof being capable of binding to the complex formed between the capture antibody (or antibody fragment) and the antigen.

The invention is disclosed in more detail in the Experimental Section.

Experimental Section

1. Production of the Osteocalcin Monoclonal Antibodies

Materials and Equipment

GST-rhOC (GST=glutathione S-transferase) used as an immunogen was produced as described (Käkönen et al. Prot Exp Purif 1996; 3: 137–44). Bovine osteocalcin (bOC) was obtained from Biodesign International, Kennebunkport, Me. Freund's complete adjuvant (Fca) and Freund's incomplete adjuvant (Fia) were obtained from Sigma Immuno Chemicals, St Louis, Mo. The Optimem-1 with glutamax-1, Dulbecco's Modified Eagle Medium (DMEM, 10x liquid), L-glutamine, sodiumpyruvate (tissue culture tested), sodiumbicarbonate (tissue culture grade) and penicillin-streptomycin (P/S) solution were purchased from Gibco BRL, Life Technologies, Grand Island, N.Y., Hepes from Boehringer Mannheim, Germany and the fetal bovine serum from Hyclone, Logan, Utah and were used as components in culture mediums. Reagents and equipment used for screening the hOC specific hybroma cell lines were obtained from Wallac Oy, Turku, Finland except the Europium-labeled hOC was prepared according to Hellman et al. (J Bone Miner Res 1996; 11: 1165–75). Tecnomouse hollow-fiber bioreactor used for the large scale production of Mabs was obtained from Integra Biosciences AG, Wallisellen, Switzerland and Protein A agarose Affigel® for the purification of the Mabs was from Bio-Rad, Richmond, Calif.

Immunization of the Mice and Screening of the hOC Specific Mabs.

The employing of recombinant OC fusion protein as an immunogen has been described earlier (Matikainen et al In "Animal cell technology: Developments towards the 21st century" 1995; pp. 475–9). Ten months old male Balb/c mouse was intraperitoneally immunized with 413 µg GST-rhOC antigen (corresponding to 75 µg of rhOC portion) mixed with Fca. The mouse was boostered 15 weeks later with 358 of the same antigen (60 µg of rhOC) mixed in Fia. The final booster dose, 110 µg antigen (20 µg of rhOC) in PBS was given i.p. after 8 weeks.

Bovine osteocalcin was coupled to keyhole limpet hemocyanin (KLH) as described (Young et al. Prostaglandines 1982; 23: 603–13). Two three-month-old Balb/c male mice were i.p. immunized with 50 µg of bOC-KLH antigen mixed with Fia. The mice were boostered with the same amount of antigen in Fia. The final booster dose, 10 µg bOC-KLH in PBS, was given intravenously.

Three days after the final booster the splenocytes were fused to mouse myeloma cells SP 2/0 as described in more detail earlier (Lilja et al. Clin Chem 1991; 37: 1618–25). The hybridomas were grown in Optimem-1 with glutamax-1 containing 20% of fetal bovine serum. The hOC specific Mabs were screened with immunofluorometric assay (IFMA) using rabbit antimouse Ig microtitration wells and hOC labeled with Europium as described earlier (Matikainen et al. 1995).

Large Scale Production and Purification of the Mabs

Before large scale production of Mabs the positive hybridomas were cloned at least twice by the limiting dilution method. Optimem-1 with glutamax-1 supplemented with 20% of fetal bovine serum was used as culture medium. Cell lines 2H9F11F8(2H9) and 6F9G4E10 (6F9) obtained from the GST-rhOC immunization and 3H8H2D2A12F12 (3H8) obtained from bOC immunization were selected for further characterization. The Mabs were produced in Tecnomouse hollow-fiber bioreactor. DMEM (1x solution) supplemented with L-glutamine, Hepes, sodiumpyruvate, sodiumbicarbonate and P/S was used as a culture medium in intracapillary circulation. Optimem-1 with glutamax-1 supplemented with 2.5% fetal bovine serum was used as a harvesting medium in extracapillary space. Produced Mabs were purified by Protein A agarose chromatography using Affigel® purification kit according to manufacturer's suggestions.

2. Epitope Mapping, Characterization of the Mabs and Two-Site Assays

Materials and Equipment

In the subclass determination of the Mabs, the streptavidin-coated microtiter plates were obtained from Wallac Oy and biotinylated rat antimouse Ig subclass specific Mabs from Serotec, Oxford, England. For epitope mapping the synthetic osteocalcin peptide 7–19 containing Glu at residue 17 was purchased from Bachem, Switzerland and bovine osteocalcin (bOC) was obtained from Biodesign International, Kennebunkport, Me. Osteocalcin from human femurs was purified by modifying a previously described method (Gundberg et al. Meth Enzymol 1984; 107: 516–544) as explained in detail by Hellman et al. (1996). Also the carboxypeptidase Y digestion, trypsin digestion, alkylation and decarboxylation of hOC has been described earlier (Hellman et al. 1996). The detailed characterization of the hOC and its modifications is described by Hellman et al. (1996). The recombinant forms of osteocalcin were produced as described earlier (Käkönen et al. Protein Expres Purif 1996; 8: 137–44).

The production and purification of a truncated form of rhOC (del. rhOC) (lacking 10 COOH-terminal amino acid residues) from a gene carrying a stop mutation in the structural region was performed under similar conditions. Both rhOC and del rhOC have an extension of three amino acid residues in their $NH_2$ termini; in addition, they lack the γ-carboxylation characteristic of hOC isolated from bone.

Reagents for biotinylation, biotin isothiocyanate (BITC) and labeling, europium(III) chelate of 4-[2(-4-isothiocyanatophenyl)ethynyl]-2,6-bis{[N,N-bis(carboxymethyl)amino]-methyl}pyridine (Takalo et al. Helv Chim Acta 1993; 76: 877–83) were from Wallac Oy. Streptavidin coated microtiter plates, Delfia® Buffer, Delfia® Wash Solution, Delfia® Enhancement Solution and Delfia® Research Fluorometer, Model 1234 used in IFMA measurements were obtained from Wallac Oy. Reagents and equipment used in the immunoassays were similar throughout the study.

Characterization of the Mabs

Labeling of the peptides for subclass determination and epitope mapping was done according to Hellman et al. 1996. The Mabs 3G8, 6F9 and 3H8 belonged to subclass IgG1 and the Mab 2H9 to subclass IgG2a as determined according to Matikainen et al., 1995.

Figure 1:
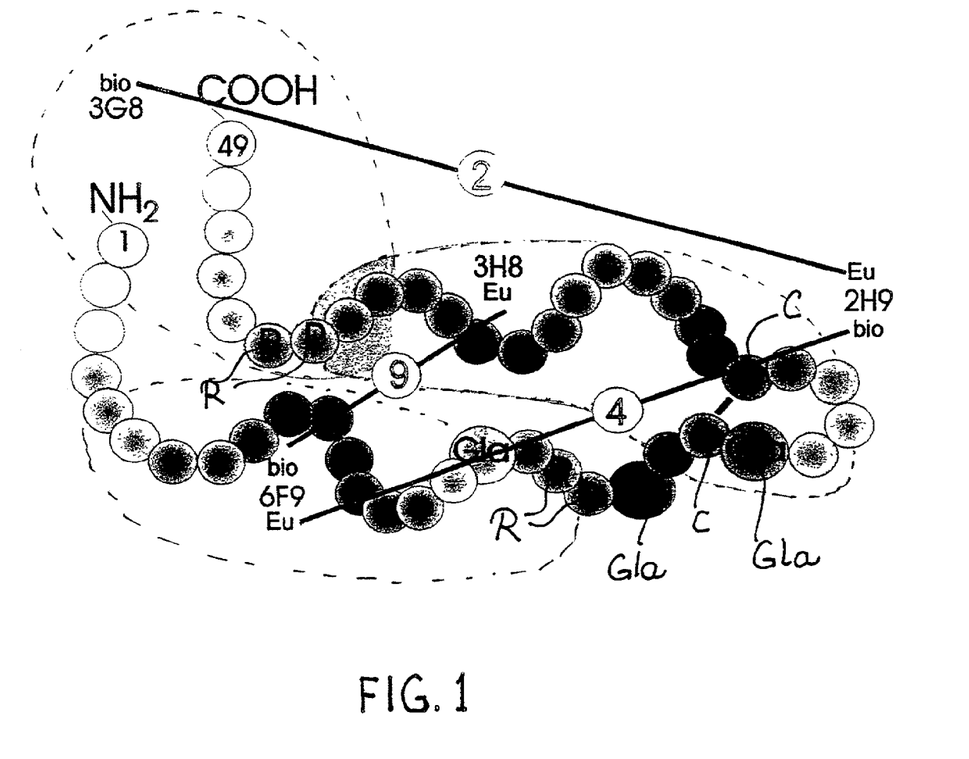
FIG. 1. A representation of the epitopes recognized by the Mabs used in two-site hOC assays. The molecule has been divided into four putative areas, each of which is being recognized by different Mabs. Amino- and carboxyterminal amino acids have been marked as 1 and 49, respectively. The protease-sensitive sites have been indicated as R—R (arginine—arginine), the three Gla-residues are shown as well as the disulphide bridge (C—C).

The Mabs were characterized for their binding to Eu-labeled intact hOC, bOC and tryptic or synthetic peptides as described (Hellman et al. 1996). The Mab 3H8 obtained by immunization with bOC conjugated to KLH recognized the tryptic 20–43 fragment. Mab 6F9 recognized the tryptic 1–19 and synthetic 7–19 peptides. Mab 2H9 recognized the tryptic 20–43 peptide. Mab 3G8 recognized only full-length unlabeled hOC and hOC when tested with two-site combinations. Summary of the Mabs in Table 1. According to information obtained an epitope map was created (FIG. 1).

Characterization of the Two-Site Assays

The two-site combinations #2, #4 and #9 were validated in more detail by determination of the crossreactivities to the alkylated hOC, decarboxylated hOC, carboxypeptidase Y-digested hOC(CPYhOC), recombinant hOC and truncated recombinant hOC. According to information obtained by crossreactivity determination and the epitope mapping the assay #2 (bio-3G8/Eu-2H9) could detect only full-length hOC (intact hOC or IOC). Assays #4 (bio-2H9/Eu-6F9) and

TABLE 1

Characterization of Mabs against hOC

| Hybridoma clone | Immunogen | Immunoglobulin class | Eu-labeled OC forms recognized | | | | | |
|---|---|---|---|---|---|---|---|---|
| | | | Eu-hOC | Eu hOC 1–19 | Eu-hOC 7–19 | Eu-hOC 15–31 | Eu-hOC 20–43 | Eu-bOC |
| 2H9 | rGST-hOC | IgG2a | + | − | − | + | + | + |
| 3H8 | bOC-KLH | IgG1 | + | − | − | + | + | + |
| 6F9 | rGST-hOC | IgG1 | + | + | + | + | − | − |
| 3G8 | bOC-KLH | IgG1 | +* | − | − | + | − | +* |

*Mab 3G8 recognizes unlabeled hOC and bOC when tested with two-site combinations.

Biotinylation and Eu Labeling of the Mabs

In order to create two-site combination assays the Mabs 3G8, 2H9, and 6F9 were biotinylated with BITC and the Mabs 2H9, 6F9, and 3H8 were labeled with europium(III) chelate in reaction conditions previously described (Hellman et al, 1996). The two-site immunoassay utilized time-resolved fluorometry using lanthanide chelate labels, like europium, as a detection system (Soini and Lövgren CRC Crit Rev Anal Chem. 1987; 18: 105–53).

9 (bio-6F9/Eu-3H8) were able to detect the full-length hOC (1–49) and also the large $NH_2$-terminal fragment (1–43). Assays #2 and #4 measured both γ-carboxylated and fully decarboxylated form of hOC. The #9 assay distinctively preferred the carboxylated form of hOC (γ-carboxylated hOC of COC). Determination of the affinity constants of labeled Mabs were done according to Hellman et al. 1996 using Scatchard analysis (Scatchard, Ann NY Acad Sci 1949; 51: 660–72). Characteristics of the assays are summarized in Table 2.

TABLE 2

Characteristics of the IFMAs #2, #4, and #9.

| Antigen | Buffer[a] | Affinity constant/ $B_{max}$[b] | #2 (bio-3G8/ Eu-2H9) | #4 (bio-2H9/ Eu-6F9) | #9 (bio-6F9 Eu-3H8) |
|---|---|---|---|---|---|
| hOC | AB + EDTA | Affinity constant | 3.4 | 0.83 | 0.64 |
| | | $B_{max}$ | 1.2 | 0.44 | 0.3 |
| | AB | Affinity constant | 3.3 | 0.7 | 0.68 |
| | | $B_{max}$ | 1.4 | 0.47 | 0.35 |
| | AB + $CaCl_2$ | Affinity constant | 4.2 | 0.42 | 0.2 |
| | | $B_{max}$ | 1.4 | 0.26 | 0.1 |
| rhOC | AB + EDTA | Affinity constant | 5.7 | 0.25 | [c] |
| | | $B_{max}$ | 0.92 | 0.17 | [c] |
| | AB | Affinity constant | 5.9 | 0.19 | [c] |
| | | $B_{max}$ | 0.94 | 0.23 | [c] |
| | AB + $CaCl_2$ | Affinity constant | 6.0 | 0.19 | [c] |
| | | $B_{max}$ | 0.92 | 0.12 | [c] |
| Cross-reactivity in percent (w/w)[d] | | hOC | 100 | 100 | 100 |
| | | dec.hOC | 64 | 46 | 8 |
| | | rhOC | 69 | 44 | 7 |
| | | CPYhOC | 9 | 150 | 156 |
| | | del.rhOC | 1 | 65 | 6 |
| | | alkyl hOC | 76 | 75 | 3 |

[a]Assay Buffer (Wallac Oy) was used as such, with 5 mM EDTA or with 25 mM $CaCl_2$.
[b]Affinity constants are expressed as value × $10^9$ L/mol and $B_{max}$ values as value × $10^{-10}$ mol/L.
[c]Affinity constant and $B_{max}$ below detectable limit.
[d]Measured as described in Hellman et al.

In addition to two-site non-competitive assays, the hOC specific antibodies could be utilized in competitive assays as a capture antibody. In competitive assay hOC forms in sample compete with the Eu-labeled hOC or hOC peptides for binding to the limited number of capture Mabs. With Mabs 2H9, and 3H8 also Eu-labeled bOC could be used due to crossreactivity explained in Table 1.

3. Optimized Assay Procedures for the Measurement of Intact, Total and γ-carboxylated OC Materials and Equipment The employed Mabs have been characterized in the previous section. In addition to Mabs produced in hybridoma cell culture, also recombinant antibody fragments could be used in the assay concept. hOC and CPYhOC used for the standardization of the assays were produced as explained in section 2. DTPA (diethylenetriaminepentaaceticacid)-treated BSA in TSA-buffer (50 mM Tris-HCl, 150 mM NaCl, 15 mM $NaN_3$, pH 7.75) used as a diluent in standardization was obtained from Wallac Oy. Materials and equipment used in the OC IFMAs have been listed in the section 2.

All-in-One Assays

10 μL of samples and standards were added into each well of streptavidin coated microtiter plates followed by a mixture of biotinylated and Eu labeled Mabs in 50 μL of Delfia® Assay Buffer containing 5 mM EDTA. The amount of capture Mab was 200 ng/well and 200 (#4) or 100 ng (#2 and #9) per well of tracer Mabs. The plates were incubated with continuous shaking at room temperature (for 2 hours) or at +35° C. (for 1 hour) followed by a six times wash with Delfia® Wash Solution. For enhancement of the Eu-chelate fluorescence, 200 μL of Delfia® Enhancement Solution per well was added after which the plates were shaken 30 min at room temperature. The signal was measured with the Delfia® Research Fluorometer (Model 1234, Wallac).

Figure 2:
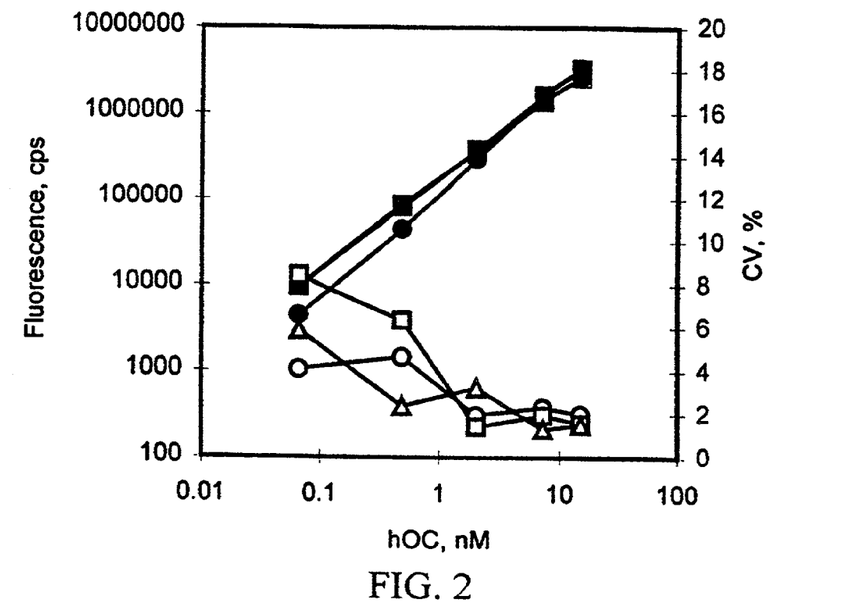
FIG. 2. Dose response curves of assays #2 (IOC, solid square), #4 (TOC, solid circle) and #9 (COC, solid triangle) given as fluorescence counts vs. hOC standard concentrations over the range (0.017, 13.5 nM) and corresponding within-assay CV:s (open symbols) calculated from 12 replicates.

All three assays enable sensitive estimation of hOC in the concentration range from 0.1–90 μg/L hOC. The precision profiles obtained from 12 replicates of each standard calibrator of each assay are presented in the FIG. 2. CVs varied between 2 to 8 percent over the standard range. The detection limits, defined as the concentration corresponding to the mean value of 12 determinations of the zero calibrator+2SD, were 0.06, 0.05 μg/L and 0.07 μg/L for the IFMAs #2, #4, and #9, respectively. The within- and between-assay variations of the assays were calculated with three serum samples containing low, medium and high concentration of hOC. The within-assay CVs were under 5% (n=12) and the between-assay CVs (n=12) were under 8% in each of the assay. The linearity of the assays was excellent as estimated by 2-, 4-, and 8-fold dilutions of five serum samples with the zero calibrator. The analytical recoveries of hOC (10, 20 and 50 μg/L as quantified by N-terminal sequencing) added to human sera (n=9) were 92±8.2%, 91±5.3% and 95±4.6% for IFMAs #4 and #9, respectively.

The characteristics of these assays have been described in detail by Käkönen et al. Clin Chem 2000; 46: 332–7.

4. Determination of Osteocalcin Concentrations in Warfarin Treated Patients

Materials and Equipment

The protocols of the OC IFMAs measuring total (#4) or γ-carboxylated hOC (#9) have been described in section 3.

Subjects and Sample Collection

The response to treatment affecting the γ-carboxylation of hOC was studied using a clinical cohort of 37 patients on continues warfarin treatment (19 women and 18 men, 73±8 years) and 30 untreated age matched controls (12 women and 18 men, 72±6 years). All the women were postmenopausal. The warfarin drug had been taken for recurrent thromboembolism or chronic heart disease for at least 12 months and the weekly dosage varied between 8.75–78.75 mg (mean 33.6). All but one of the patients had therapeutic prothrombin (PT) levels with an INR (international normalized ratio) of 2.0–3.8 as measured by Prothrombin complex test (SPA 50, Diagnostic Stago, France). One patient was on a fixed minidose of warfarin (1.25 mg/day) and had a normal PT level. The hOC concentration in the serum samples was measured with OC IFMAs #4 and #9. Warfarin panel was collected in Malmö University Hospital, Sweden and the study was approved in all parts by the local ethical committee. Detailed information of this panel has been reported by Obrant et al. J Bone Miner Res; 1999; 14: 555–60.

Total and γ-carboxylated Osteocalcin in Warfarin Treated Subjects

Figure 3:
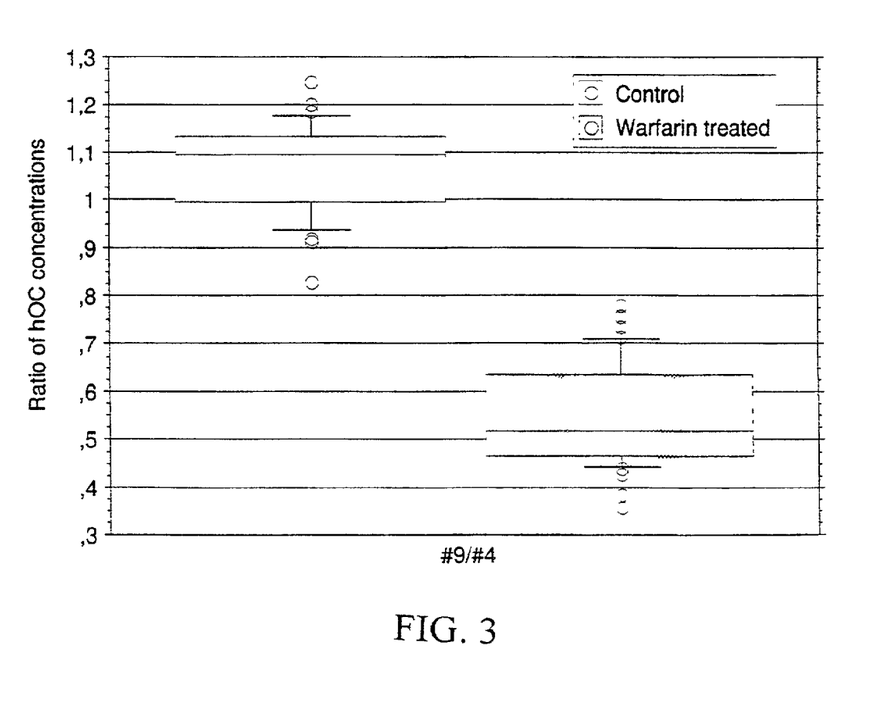
FIG. 3. The COC/TOC (#9/#4) and COC/IOC (#9/#2) concentration ratios in warfarin-treated (n=37) and control subjects (n=30). The horizontal lines of the box plots represent the 10th, 25th, 50th, 75th, and 90th percentiles.

The concentration of hOC as measured with assay #9 was lower in the warfarin treated patients when compared to the control patients (Table 3.). Conversely, there was no significant difference between the warfarin treated patients and the controls in the amount of total hOC measured by assay #4. Furthermore, the proportion of carboxylated hOC/total hOC was remarkably low in the warfarin treated patients compared to the controls (p<0.0001) and a single cut-off level of 0.8 fully separated the two patient groups (FIG. 3.).

TABLE 3

Serum levels of total and y-carboxylated hOC and the ratio γ-carboxylated to total hOC in 37 warfarin treated patients and 30 control patients (mean ± SD).

| | total OC (#4) (ng/mL) | carboxylated OC (#9) (ng/mL) | carboxylated OC/ total OC |
|---|---|---|---|
| warfarin-treated patients | 9.4 ± 8.9 | 4.9 ± 3.8 | 0.55 ± 0.11 |
| control patients | 12.7 ± 10.6 | 13.1 ± 9.7 | 1.07 ± 0.09 |
| level of significance | n.s. | p < 0.0001 | p < 0.0001 |

5. Determination of Osteocalcin Concentrations in Elderly People

Materials and Equipment

The protocols of the OC IFMAs measuring intact, total or γ-carboxylated hOC have been described in section 3.

Subjects and Sample Collection

The population consisted of all home-dwelling persons aged 70 years or over who lived in five rural municipalities around the city of Oulu in northern Finland on Sep. 1, 1991 (N=954). Baseline examinations were carried out during Sep. 1, 1991 to Feb. 29, 1992 by two teams consisting of a physician, two nurses and a physiotherapist. Seven hundred and ninety-two (87% of those alive at the mid-point of the examinations) participated in these examinations and the recording of falls. The characteristics of the population are described in Table 4. Based on data from the medical records, the characteristics of those who did not participate (53 men and 64 women) did not differ from those of the participants in terms of age; men 75.5 years (SD 4.8), women 76.9 years (5.3); living alone (43%); and inability to go out (11%).

TABLE 4

Characteristics of the study population (N = 792)

| Characteristic | Men (N = 301) | Women (N = 491) |
|---|---|---|
| Age, years (mean, SD) | 75.5 (4.9) | 76.5 (4.9) |
| BMI, kg/m² (mean, SD) | 26.8 (3.8) | 29.1 (5.2) |
| Unable to go out (%) | 6 | 11 |
| Poor self-rated health (%) | 23 | 22 |
| *MMSE result ≦ 23 (%) | 32 | 31 |
| No outdoor work activities (%) | 28 | 46 |
| Use of oestrogen (%) | 0 | 1 |

*MiniMental State Examination

The research teams collected the data by means of postal questionnaires, interviews, clinical examinations and clinical tests (Luukinen et al., J Am Geriatr Soc 1997; 45: 1302–9; Koski et al., Age Aging 1996; 25: 29–38). The nurses collected serum samples, which were stored after centrifugation at −72° C. The samples were measured with the OC IFMAs #2, #4 and #9. The analysis of serum samples was blind as regards the recording of falls.

Recording of falls was arranged as described in earlier reports, and lasted from the day of serum collection until Dec. 31, 1996. The occurrence of fractures was checked from the medical records at the end of each follow-up year (Luukinen et al., J Am Geriatr Soc 1997; 45: 1302–9; Luukinen et al., J Am Geriatr Soc 1995; 43: 871–6). Hip fractures totalled 26, wrist fractures 21, and other fractures 65.

hOC Concentrations in Elderly People

The distributions of intact hOC, total hOC, COC and the ratios COC/IOC and COC/TOC by age and sex are described in Table 5. Concentrations of IOC did not increase with advancing age in men (Kruskal-Wallis Chisquare=5.51 Df=3, p= 0.1383), but increased in women (Kruskal-Wallis Chisquare=30.99, df=3, p= 0.0001), and were higher in women than men (Kruskal-Wallis Chisquare=25.1 df= 1, p=0.0001). Concentrations of TOC increased with advancing age in men (ANOVA p=0.009) and women (p<0.001), and were higher in women than men (Kruskal-Wallis p<0.001). Concentrations of COC also increased with advancing age in both men (ANOVA p=0.012) and women (p<0.001), and were higher in women than men (Kruskal-Wallis p<0.001). There was no difference in the COC/IOC values between the age groups in men (Kruskal-Wallis Chisquare=3.73 df=3, p=0.2916), but concentrations decreased with age in women (Kruskal-Wallis Chisquare=18.59 df=3, p=0.0003). The COC/IOC values were higher in men than women (Kruskal-Wallis Chisquare=6.26 df=1, p=0.0124). There was no difference in the COC/TOC values between the age groups, in either men (ANOVA p=0.587) or women (p=0.250), but again the COC/TOC values were higher in men than women (Kruskal-Wallis p<0.001).

TABLE 5

Distributions (mean, SD) of intact (IOC), total (TOC), and carboxylated (COC) osteocalcin concentrations (μg/L) and the COC/TOC ratio in older persons by sex and age

| Age and sex (N) | TOC mean (SD) | COC mean (SD) | COC/TOC mean (SD) |
|---|---|---|---|
| All (792) | 10.83 (6.20) | 9.21 (4.59) | 0.94 (0.40) |
| Men (301) | 9.31 (4.62) | 8.41 (4.06) | 0.95 (0.31) |
| 70–74y. (142) | 8.99 (4.64) | 8.43 (4.35) | 0.97 (0.28) |
| 75–79y. (85) | 8.64 (4.27) | 7.45 (3.49) | 0.91 (0.34) |
| 80–84y. (54) | 10.20 (4.19) | 9.14 (3.58) | 0.95 (0.29) |
| 85+y. (20) | 12.04 (5.91) | 10.30 (4.64) | 0.98 (0.46) |
| Women (491) | 11.77 (6.84) | 9.71 (4.83) | 0.93 (0.45) |
| 70–74y. (176) | 10.17 (6.01) | 8.93 (4.19) | 0.98 (0.39) |
| 75–79y. (160) | 11.54 (6.30) | 9.45 (4.64) | 0.91 (0.48) |
| 80–84y. (109) | 12.74 (7.02) | 10.34 (5.17) | 0.89 (0.40) |
| 85+y. (46) | 16.36 (8.69) | 12.19 (6.09) | 0.88 (0.58) |

| Age and sex (N) | IOC mean (SD) | COC mean (SD) | COC/IOC mean (SD) |
|---|---|---|---|
| All (775) | 7.21 (4.39) | 9.21 (4.59) | 1.49 (0.93) |
| Men (294) | 6.17 (3.23) | 8.41 (4.06) | 1.56 (1.09) |
| 70–74y. (138) | 6.13 (3.06) | 8.43 (4.35) | 1.54 (1.06) |
| 75–79y. (83) | 5.77 (3.29) | 7.45 (3.49) | 1.42 (0.63) |
| 80–84y. (53) | 6.47 (3.00) | 9.14 (3.58) | 1.69 (1.29) |
| 85+y. (20) | 7.27 (4.41) | 10.30 (4.64) | 1.98 (1.87) |
| Women (481) | 7.85 (4.85) | 9.71 (4.83) | 1.45 (0.82) |
| 70–74y. (176) | 6.68 (3.88) | 8.93 (4.19) | 1.58 (0.84) |
| 75–79y. (157) | 7.63 (4.62) | 9.45 (4.64) | 1.38 (0.69) |
| 80–84y. (107) | 8.72 (5.27) | 10.34 (5.17) | 1.36 (0.80) |
| 85+y. (41) | 11.18 (6.20) | 12.19 (6.09) | 1.42 (1.13) |

In men, COC, COC/IOC and COC/TOC values were lower in fracture cases than controls, but no difference was found with regard to TOC or IOC. Concentrations of TOC and IOC were higher, and again COC/IOC and COC/TOC values lower in the female population with fractures than in their controls, but the corresponding COC values did not differ (Table 6).

TABLE 6

Distributions (mean, SD) of intact osteocalcin (IOC), total osteocalcin (TOC), carboxylated osteocalcin (COC) (μg/L) and the IOC/COC and COC/TOC ratios in fracture cases and controls among home-dwelling older men and women

| Sex and osteocalcin form | Fracture cases | | Controls | | |
|---|---|---|---|---|---|
| | N | mean (SD) | N | mean (SD) | p* |
| Men | | | | | |
| IOC | 21 | 6.54 (3.44) | 274 | 6.14 (3.22) | 0.587 |
| TOC | 21 | 9.45 (4.76) | 280 | 9.30 (4.69) | 0.786 |
| COC | 21 | 6.66 (4.22) | 279 | 8.54 (4.03) | 0.021 |
| COC/IOC | 21 | 1.06 (0.48) | 273 | 1.60 (1.11) | 0.001 |
| COC/TOC | 21 | 0.74 (0.36) | 279 | 0.96 (0.30) | 0.002 |
| Women | | | | | |
| IOC | 85 | 8.82 (5.30) | 401 | 7.64 (4.73) | 0.011 |
| TOC | 85 | 13.45 (7.56) | 406 | 11.42 (6.63) | 0.006 |
| COC | 84 | 9.17 (5.32) | 403 | 9.82 (4.72) | 0.073 |
| COC/IOC | 83 | 1.18 (0.70) | 398 | 1.51 (0.83) | <0.001 |
| COC/TOC | 84 | 0.77 (0.46) | 403 | 0.96 (0.44) | <0.001 |

*Kruskal-Wallis test

The incidence rates and relative risks of fracture according to higher (≧+1SD from the mean) IOC or TOC, lower (≦−1SD from the mean) COC and lower (≦−1SD from the mean) COC/IOC and COC/TOC are described in Table 7. A higher IOC or TOC value were not associated with the occurrence of fracture, but lower values of COC, COC/IOC, and COC/TOC were positively associated. Dichotomized at −1SD from the mean of the total study population, the crude relative risk of fracture as regards a low COC/IOC and COC/TOC ratio was 2.31 (1.29–4.13) and 3.47 (2.23–5.42), respectively.

TABLE 7

Incidence (/1000 person years) and crude (HRcr, 95% CI) and adjusted (HRadj, 95% CI) relative risk of fracture by intact osteocalcin (IOC), total osteocalcin (TOC), carboxylated osteocalcin (COC) and carboxylated/intact osteocalcin (COC/IOC) and carboxylated/total osteocalcin (COC/TOC) in older persons (N = 792)

| Osteocalcin form | | Fractures | | | |
| --- | --- | --- | --- | --- | --- |
| (cut-off point) | | N | Incidence | HRcr (95% CI) | Hradj* (95% CI) |
| IOC | (≧1SD) | 14 | 39 | 1.23 (0.70–2.15) | 1.00 (0.54–1.86) |
| IOC | (<1SD) | 91 | 32 | 1.0 (ref.) | 1.0 (ref.) |
| TOC | (≧1SD) | 13 | 39 | 1.22 (0.68–2.17) | 1.09 (0.57–2.07) |
| TOC | (<1SD) | 93 | 32 | 1.0 (ref.) | 1.0 (ref.) |
| COC | (≦−1SD) | 21 | 53 | 1.77 (1.10–2.86) | 2.00 (1.20–3.36) |
| COC | (>−1SD) | 84 | 30 | 1.0 (ref.) | 1.0 (ref.) |
| COC/IOC | (≦−1SD) | 13 | 70 | 2.31 (1.29–4.13) | 2.47 (1.32–4.64) |
| COC/IOC | (>−1SD) | 91 | 31 | 1.0 (ref.) | 1.0 (ref.) |
| COC/TOC | (≦−1SD) | 26 | 93 | 3.47 (2.23–5.42) | 5.32 (3.26–8.68) |
| COC/TOC | (>−1SD) | 79 | 27 | 1.0 (ref.) | 1.0 (ref.) |

SD from the mean was calculated within each 5-year age group (70–74, 75–79, 80–84 and 85+) separately in men and women (Table 2).
*adjusted for age, sex, habit of doing heavy outdoor work, ability to go out unassisted, ability to carry a 5 kg load 100 metres, body mass index, fear of falling, stroke, knee extension strength, cognitive status, visual acuity, peak expiratory flow, use of psychotropic medication, use of anit-Parkinson medication.

The following baseline variables were associated (p<0.05) with the occurrence of fracture during the five year follow-up period: higher (for the 5-year increase) age (HR 1.35), female sex (2.44), doing heavy outdoor work (0.50), inability to go out unassisted (2.28), inability to carry a 5 kg load 100 meters (2.28), poor distant visual acuity (2.65), reduced knee extension strength (2.64), frequent fear of falling (2.86), low (≦−1SD from the mean) peak expiratory flow (1.81), low cognitive status (MiniMental State Examination test result≦23 points) (1.58), past stroke (4.35), use of anti-Parkinson medication (3.78) and use of psychotropic medication (2.08). After entering these variables in Cox regression analyses, low COC and COC/TOC predicted the occurrence of fracture, but IOC and TOC did not (Table 7). The high fracture risk associated with low COC concentrations and low COC/IOC or COC/TOC ratios increased after adjusting for other risk factors of fracture, indicating independent contributions.

Dichotomized at −1 SD from the mean of the total study population, the adjusted relative risk of fracture as regards a low COC/TOC ratio was 3.26 (2.01–5.25). In the younger population (70–79 years) the multivariable-adjusted relative risks of fracture as regards high (≧1 SD) IOC, TOC, low COC, low COC/IOC, and low COC/TOC were 0.63 (0.27–1.46), 1.34 (0.60–3.00), 2.04 (1.12–3.73), and 2.31 (1.16–4.61) and 4.36 (2.46–7.75), respectively. The corresponding figures in the older (≧80 years) population were 1.05 (0.39–2.82), 1.44 (0.51–4.11), 1.51 (0.50–4.59), 2.64 (0.58–12.13) and 7.02 (2.42–20.39).

The increased risk of fracture associated with low COC/TOC found in our study resembles in magnitude the relative risk of hip fracture presented previously as regards a combination of low bone mineral density and osteocalcin with decreased carboxylation (Vergnaud P et al., J Clin Endocrinol Metab 1997; 82: 719–24). We found the increased risk of fracture with low COC/TOC to be especially high among the oldest persons, which is in line with the finding that high under-carboxylated osteocalcin predicts hip fractures (Vergnaud P et al.). According to our results, simple immunoassays for intact, total and carboxylated osteocalcin are likely to prove to be efficient tools in the short-term assessment of fracture risk among the elderly.

What is claimed is:

1. A method for the assessment of bone fragility and fracture risk, or osteoporosis, in a person, comprising the steps of
   a) measuring the concentration of gamma-carboxylated osteocalcin (COC in the body fluid sample of the said person) in the presence of EDTA by means of at least one monoclonal or polyclonal antibody or fragment thereof, said antibody or fragment
      i) is specific for gamma-carboxylated osteocalcin,
      ii) recognizes either an epitope occurring in the region of the amino acids 17–24 of the gamma-carboxylated osteocalcin molecule or the tertiary structure associated with the gamma-carboxylated osteocalcin, and
      iii) has specificity for gamma-carboxylated osteocalcin that is dependent on the presence of bivalent metal ions, said specificity is decreased in the presence of said metal ions; and optionally measuring the concentration of intact osteocalcin (IOC) or total osteocalcin (TOC) in a body fluid sample of said person and determining the ratio of COC to IOC(COC/IOC ratio) or the ratio of COC to TOC(COC/TOC ratio), and
   b) comparing
      i) the concentration of gamma-carboxylated osteocalcin (COC) for said person to the mean concentration of gamma-carboxylated osteocalcin (mean COC) in similar body fluid samples of the population of the same age and sex, or ii) the COC/IOC ratio or COC/TOC ratio for said person to the mean COC/IOC ratio or mean COC/TOC ratio, determined from measurements in similar body fluid samples of the population of the same age and sex, whereby i) a COC for said person that is lower than the mean COC is an indication of osteoporosis, bone fragility or increased risk of bone fracture in said person, or ii) a COC/IOC ratio or a COC/TOC ratio for said person that is lower than the mean COC/IOC ratio or mean COC/TOC ratio is an indication of osteoporosis, bone fragility or increased risk of bone fracture in said person.

2. The method according to claim 1 wherein the body fluid sample is a serum, plasma or urine sample.

3. The method according to claim 1 wherein COC is measured by means of one monoclonal antibody or fragment thereof, or a mixture of several monoclonal antibodies or fragments thereof.

4. The method according to claim 1 wherein the antibody fragment is a recombinantly or proteolytically produced antibody fragment.

5. The method according to claim 2 wherein COC is measured by means of one monoclonal antibody or fragment thereof, or a mixture of several monoclonal antibodies or fragments thereof.

6. The method according to claim 2 wherein the antibody fragment is a recombinantly or proteolytically produced antibody fragment.

7. The method according to claim 3 wherein the antibody fragment is a recombinantly or proteolytically produced antibody fragment.

8. The method according to claim 5 wherein the antibody fragment is a recombinantly or proteolytically produced antibody fragment.

* * * * *